US011993267B2

(12) United States Patent
Brooks et al.

(10) Patent No.: US 11,993,267 B2
(45) Date of Patent: May 28, 2024

(54) ALERTER AUGMENTATION SYSTEM

(71) Applicant: Transportation IP Holdings, LLC, Norwalk, CT (US)

(72) Inventors: James Brooks, Niskayuna, NY (US); Lalit Keshav Mestha, Niskayuna, NY (US)

(73) Assignee: Transportation IP Holdings, LLC, Norwalk, CT (US)

( * ) Notice: Subject to any disclaimer, the term of this patent is extended or adjusted under 35 U.S.C. 154(b) by 958 days.

(21) Appl. No.: 16/410,255

(22) Filed: May 13, 2019

(65) Prior Publication Data

US 2019/0263416 A1    Aug. 29, 2019

Related U.S. Application Data

(63) Continuation of application No. 15/397,545, filed on Jan. 3, 2017, now Pat. No. 10,328,946.

(51) Int. Cl.
| | |
|---|---|
| *B60W 40/08* | (2012.01) |
| *A61B 5/18* | (2006.01) |
| *B60W 50/08* | (2020.01) |
| *B60W 50/14* | (2020.01) |
| *B60W 60/00* | (2020.01) |
| *B60W 50/00* | (2006.01) |

(52) U.S. Cl.
CPC ............... *B60W 40/08* (2013.01); *A61B 5/18* (2013.01); *B60W 50/082* (2013.01); *B60W 50/14* (2013.01); *B60W 60/0018* (2020.02); *B60W 60/0051* (2020.02); *B60W 60/0053* (2020.02); *B60W 60/0059* (2020.02); *B60W 2040/0818* (2013.01); *B60W 2050/0075* (2013.01); *B60W 2050/143* (2013.01); *B60W 2540/221* (2020.02); *B60W 2540/223* (2020.02); *B60W 2540/229* (2020.02); *B60W 2556/10* (2020.02)

(58) Field of Classification Search
CPC ............ G08B 21/06; B60W 2040/0818–0872; B60W 40/08; B60W 40/09; B60W 50/082; B60W 50/14; B60W 50/16; B60W 2050/143; B60W 2050/146; A61B 5/18; B60K 28/02; B60K 28/06
See application file for complete search history.

(56) References Cited

U.S. PATENT DOCUMENTS

| | | | | |
|---|---|---|---|---|
| 9,925,872 | B1 * | 3/2018 | Alasry | B60W 50/12 |
| 10,328,946 | B2 * | 6/2019 | Brooks | B60W 50/082 |
| 2009/0267777 | A1 * | 10/2009 | Kumar | G08B 21/06 |
| | | | | 340/576 |
| 2012/0212353 | A1 * | 8/2012 | Fung | G01C 21/3697 |
| | | | | 340/905 |

* cited by examiner

*Primary Examiner* — Spencer D Patton
(74) *Attorney, Agent, or Firm* — K&L Gates LLP

(57) ABSTRACT

An alerter augmentation system includes one or more processors that determine an alertness of an operator of a vehicle system. The one or more processors also generate operator input requests that are separated in time by a temporal delay. These input requests seek responses or action by the operator in an attempt to keep or make the operator alert. The one or more processors change one or more of the temporal delay between the input requests and/or a type of the input requests that are generated based at least in part on the alertness of the operator that is determined.

20 Claims, 3 Drawing Sheets

ALERTER AUGMENTATION SYSTEM

CROSS-REFERENCE TO RELATED APPLICATION

This application is a continuation of U.S. patent application Ser. No. 15/397,545, filed 3 Jan. 2017, the entire disclosure of which is incorporated herein by reference.

FIELD

Embodiments of the present disclosure generally relate to systems that monitor alertness of operators of machinery (e.g., vehicles) and that implement responsive actions based on the alertness of the operators.

BACKGROUND

Some machinery includes alerter systems that periodically prompt operators of the machinery for a response. For example, some vehicles may prompt drivers of the vehicles to depress a button at regular time intervals to try and ensure that the drivers are alert during control of the vehicles.

These alerter systems may provide the prompts for operator action on a regular, unchanging basis with respect to time. For example, a prompt may be provided every minute or several minutes. Other alerter systems may provide the prompts at a frequency that is based on how fast a vehicle is moving. The prompts may be provided at a more rapid rate or greater frequency for faster speeds of the vehicles and at slower rates or reduced frequencies for slower speeds of the vehicles.

Operators who are alert may find the prompts unnecessarily intrusive and obstructive to control of the vehicles. The requirement to repeatedly respond to the prompts even considering the operators being aware can serve as an additional distraction to the same operation of the vehicles.

BRIEF DESCRIPTION

In one embodiment, a system (e.g., an alerter augmentation system) includes one or more processors configured to determine an alertness of an operator of a vehicle system. The one or more processors also are configured to generate operator input requests that are separated in time by a temporal delay, the one or more processors configured to change one or more of the temporal delay between the input requests or a type of the input requests that are generated based at least in part on the alertness of the operator that is determined.

In one embodiment, a method (e.g., for augmenting operation of an alerter system) includes determining an alertness of an operator of a vehicle system using a monitoring system, and changing one or more of a temporal delay between successive input requests provided by an alerter system of the vehicle system or a type of the input requests provided by the alerter system based at least in part on the alertness of the operator that is determined.

In one embodiment, a system (e.g., an alerter augmentation system) includes one or more processors configured to automatically instruct an alerter system to generate requests for operator input at time intervals in order to maintain an alertness of an operator controlling a powered system. The one or more processors also are configured to direct the alerter system to one or more of change the time intervals between the requests or change a type of the requests responsive to a change in the alertness of the operator.

BRIEF DESCRIPTION OF THE DRAWINGS

The subject matter described herein will be better understood from reading the following description of non-limiting embodiments, with reference to the attached drawings, wherein below.

DETAILED DESCRIPTION

One or more embodiments of the inventive subject matter described herein provide systems and methods that augment alerter systems in machinery that is at least partially operated by human operators. The systems and methods described herein can obtain information on how alert an operator is and, based on the alertness or non-alertness of the operator, the systems and methods can change how the alerter system operates. For example, the augmentation systems and methods described herein can receive data indicative of an alertness of the operator. This data (also referred to as alertness data) can indicate a quantifiable score or value representative of how alert the operator is. Different values for the alertness data can indicate different levels of operator alertness, and changes in the values of the alertness data can indicate changes in how alert an operator is.

The augmentation systems and methods can change the frequency (or rate) and/or type of alerts provided by the alerter system based on the alertness of the operator (and/or based on changes in the alertness of the operator). For example, if the operator is more alert or the alertness of the operator increases, then the temporal (e.g., time) delay or time interval between successive prompts provided by the alerter system for operator interaction or input may increase. Fewer or less frequent alerts may need to be provided to the operator due to the increased alertness of the operator. In contrast, if the operator is less alert or the alertness of the operator decreases, then the temporal delay between successive prompts for operator input may decrease. More frequent alerts may need to be provided to the operator due to the decreased alertness of the operator.

The type of alertness (e.g., prompt for operator input) provided by the alerter system may be changed by the augmentation systems and methods based on the operator alertness. For example, if the operator is more alert or the alertness of the operator increases, then the prompts for operator input provided by the alerter system may remain or be changed to visual prompts, such as the flashing of a light, text or other indicium presented on a display device, etc. If the operator is less alert or the alertness of the operator decreases, then the prompts for operator input may be changed to audible prompts (such as loud alarms or bells), haptic prompts (e.g., the vibrating of an operator seat or control), and/or a combination of visual, audible, and/or haptic prompts.

Figure 1:
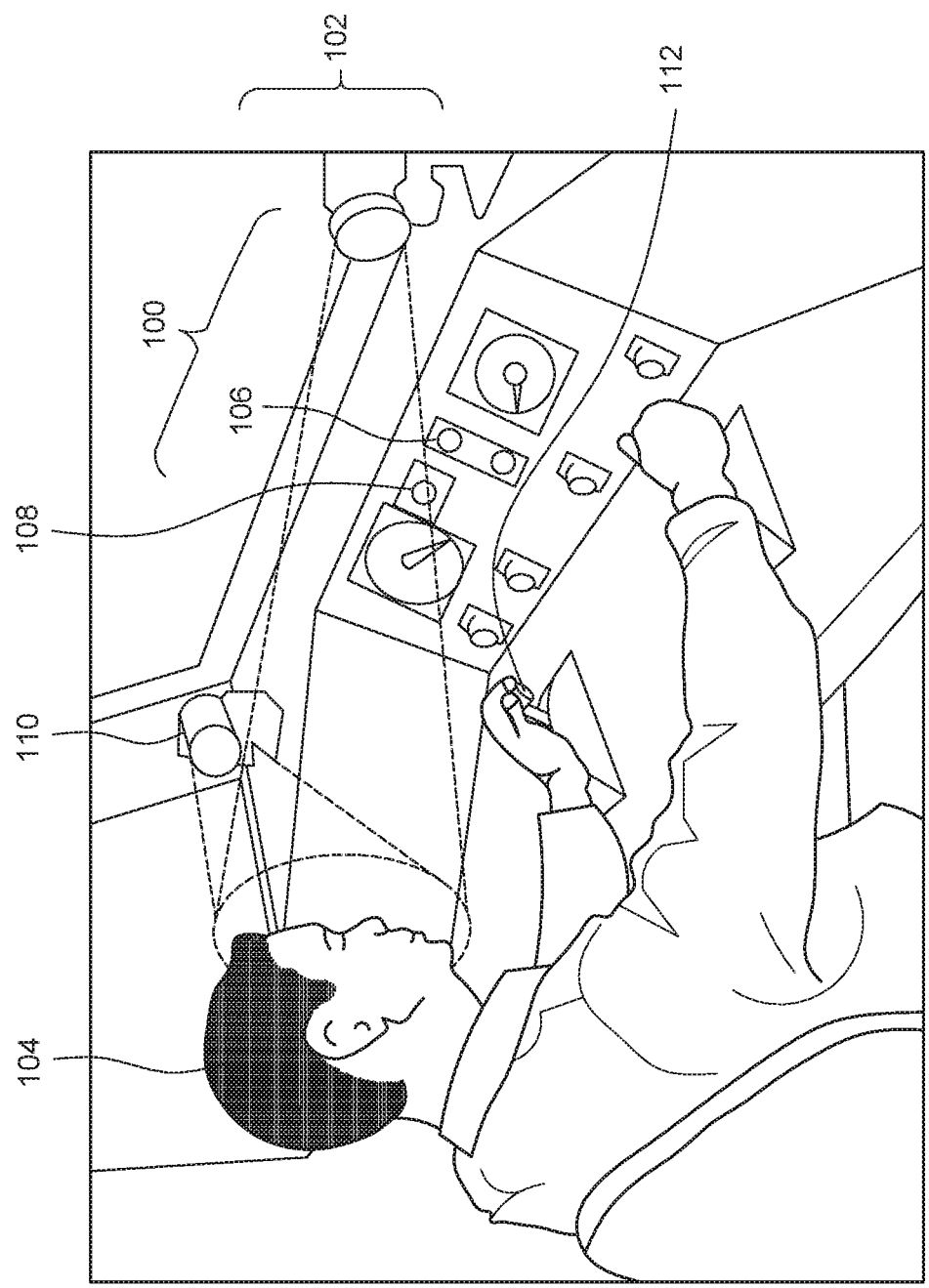
FIG. 1 illustrates one embodiment of an alerter system and a monitoring system.

FIG. 1 illustrates one embodiment of an alerter system 100 and a monitoring system 102. The alerter system 100 provides prompts to an operator 104 of machinery, such as a vehicle (also referred to as a vehicle system), stationary powered system, or the like. The alerter system 100 can provide visual prompts by flashing one or more light generating devices 106, by displaying information on a display device 108, by turning off or on the light in the cabin or room in which the operator 104 is located, by changing a color of the light in the cabin or room in which the operator 104 is located, or the like. The alerter system 100 can include and/or be operably connected with (e.g., via one or more wired and/or wireless connections) one or more input devices 112. The input device 112 can include buttons, touchscreens, pedals, levers, switches, keys, or the like, that are actuated by the operator 104. The alerter system 100 can determine if the operator actuates the input device 112 responsive to providing an alert or prompt. If the input device 112 is actuated, the alerter system 100 may provide an additional prompt or alert at a later time. If the input device 112 is not actuated in response to the alert or prompt, then the alerter system 100 may automatically implement one or more responsive actions, such as slowing or stopping movement of the vehicle, turning off the powered system controlled by the operator, or the like.

The monitoring system 102 includes one or more sensors 110, such as cameras that obtain images or video of the operator 104 to extract various physical (such as specific micro-expression associated with nuanced muscle movement, macro-expressions, eye closure (blink-rates), head nodding, and yawning etc., thermal (e.g., infrared) sensors to obtain thermal imagery of the face of the operator, or the like. The monitoring system 102 examines the information obtained or sensed by the sensors 110 to extract various physical and psychophysiological features (pulse rate, respiration rate, heart rate variability, peak-to-peak amplitudes, power in harmonics, deep learning, etc.). This information is used by the monitoring system 102 to estimate fatigue and drowsiness of the operator, which is represented by an alertness score generated by the monitoring system 102. The monitoring system 102 can determine the alertness of the operator based on one or more differences between a current operator behavior and a historical operator behavior. For example, if an operator begins to drop his or her shoulders or otherwise change posture, yawn, close his or her eyes, etc., then the monitoring system 102 may determine that the operator is less alert. One example of such a monitoring system 102 is described as a control system in U.S. patent application Ser. No. 15/397,469, the entire disclosure of which is incorporated herein by reference.

Based on the alertness of the operator as determined by the monitoring system 102, an alerter augmentation system (shown and described below) can change how the operator input prompts (e.g., alerts) generated by the alerter system 100 are presented to the operator.

Figure 2:
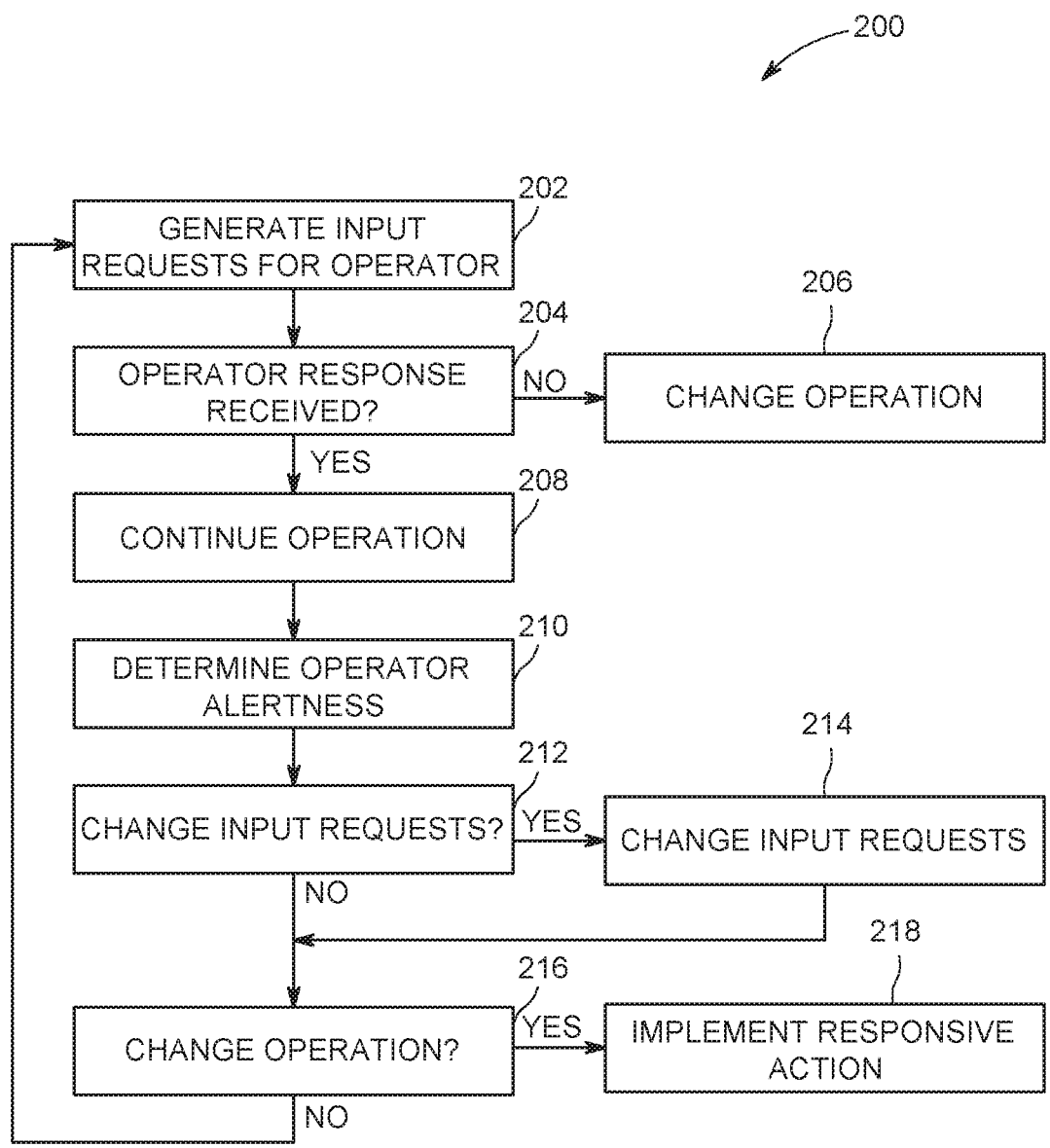
FIG. 2 illustrates a flowchart of one embodiment of a method for augmenting an alerter system of a powered system.

FIG. 2 illustrates a flowchart of one embodiment of a method 200 for augmenting an alerter system of a powered system. The method 200 may represent at least some of the operations performed by the alerter augmentation system described herein, and can represent operations performed by one or more software applications directing the functions of the alerter augmentation system. Optionally, the method 200 may represent an algorithm used to create such software applications.

At 202, one or more operator input requests are generated. The input requests may be referred to as alerts or prompts. The input requests are generated by the alerter system 100, and can include visual, audible, and/or haptic alerts provided via the alerter system 100, as described above. The input requests may be repeatedly provided by the alerter system 100. For example, the alerter system 100 may activate a light, generate a sound, or the like, once every five minutes to ensure that the operator remains alert during operation of the powered system.

At 204, a determination is made as to whether a response to an input request is received from the operator in response to generation of an input request. For example, the alerter system 100 may determine whether the operator has actuated the input device 112 within a designated period of time (e.g., five seconds) following generation or provision of the previous input request by the alerter system 100. If an operator response to the previous input request is not received or detected by the alerter system 100, then the lack of a response may indicate that the operator is not alert. As a result, flow of the method 200 may proceed toward 206. But, if an operator response is received, then the response can indicate that the operator is at least alert enough to respond to the input request. As a result, flow of the method 200 can proceed toward 208.

At 206, operation of the powered system may change. If the powered system is a vehicle, then the alerter system 100 may automatically engage a brake system of the vehicle to slow or stop movement of the vehicle. If the powered system is another type of machine or system of machines, then the alerter system 100 may deactivate or turn off the powered system or otherwise change operation of the powered system to a state where the lack of an operator or lack of an alert operator poses little to no risk of safety or harm to the operator or others. Flow of the method 200 may then terminate or return to another operation, such as 202.

At 208, operation of the powered system may continue. For example, in contrast to slowing or stopping a vehicle or deactivating the powered system, the powered system may continue to operate as before because the operator responded to the input request previously provided.

At 210, alertness of the operator is determined. The monitoring system 102 can determine an alertness score (or rating, value, or the like) that indicates how alert the operator is. For example, the monitoring system 102 can determine how alert an operator is using one or more embodiments of the control systems and methods described in U.S. patent application Ser. No. 15/397,469, entitled "Systems and Methods for Voltage Sensing" filed 3 Jan. 2017.

Optionally, the alertness of the operator may be determined based on responses of the operator to one or more previous input requests. For example, operators that respond within a designated period of time to more input requests may have a greater alertness score than operators responding to fewer input requests within the designated period of time.

At 212, a determination is made as to whether the input requests provided to the operator are to be changed. If the operator is alert (as indicated or determined from the alertness determined at 210), then the frequency at which the input requests are provided to the operator may be able to be decreased. For example, the alerter system 100 may be able to delay the time between when successive input requests are generated due to the operator being alert or more alert. As another example, the alerter system 100 may be able to provide a different type of alert, such as an alert that is not as loud or bright, to the operator due to the operator being alert or more alert. The frequency and/or type of alert may be changed so as to avoid unnecessarily obstructing or interfering with the tasks performed by the alert operator.

If the operator is not alert (as indicated or determined from the alertness determined at 210), then the frequency at which the input requests are provided to the operator may be increased. For example, the alerter system 100 may shorten the time between when successive input requests are generated due to the operator not being alert or being less alert. As another example, the alerter system 100 may be able to provide a different type of alert, such as an alert that is louder or brighter than one or more previous alerts. The frequency and/or type of alert may be changed so as to try and increase the alertness of the operator.

The determination of whether or not to change the alertness of the operator may be made by comparing the alertness score or data determined by the monitoring system 102 to a designated threshold and/or to a previous alertness score. If the alertness score of the operator is less than the threshold and/or is less than the previous alertness score, then flow of the method 200 may proceed toward 214. If the alertness score of the operator is at least as large as the threshold and/or is at least as great as the previous alertness score, then flow of the method 200 may proceed toward 216.

At 214, the input requests provided by the alerter system are changed. The augmentation system may direct the alerter system to change the input requests by communication of one or more control signals from the augmentation system. In one aspect, the control signals may be automatically generated and communicated by the augmentation system responsive to determining that the alertness of the operator is too low (e.g., as determined at 212). In response to receiving these directions from the augmentation system, the alerter system 100 may change the input requests provided to the operator. In one embodiment, the alerter system 100 can change the frequency at which the input requests are provided. This can be accomplished by the alerter system 100 reducing the temporal delay between when successive input requests are generated, thereby causing the input requests to be provided more often. Optionally, the alerter system 100 can change the type of input requests provided to the operator. For example, the alerter system 100 may increase the volume, pitch, etc., of sounds generated; increase the brightness, intensity, color, etc. of lights generated; change the text or images displayed; increase the magnitude and/or frequency of vibrations generated; or the like. As another example, the alerter system 100 can change a combination of input requests that are provided. If the alerter system 100 previously was providing visual input requests, then the alerter system 100 may begin providing visual, audible, and/or haptic requests.

In another aspect, the control signals may be automatically generated and communicated by the augmentation system responsive to determining that the operator is alert or is more alert than before (e.g., as determined at 212). In response to receiving these directions from the augmentation system, the alerter system 100 may change the input requests provided to the operator. In one embodiment, the alerter system 100 can change the frequency at which the input requests are provided. This can be accomplished by the alerter system 100 increasing the temporal delay between when successive input requests are generated, thereby causing the input requests to be provided less often. Optionally, the alerter system 100 can change the type of input requests provided to the operator. For example, the alerter system 100 may decrease the volume, pitch, etc., of sounds generated; decrease the brightness, intensity, color, etc. of lights generated; change the text or images displayed; reduce the magnitude and/or frequency of vibrations generated; or the like. As another example, the alerter system 100 can change a combination of input requests that are provided. If the alerter system 100 previously was providing a combination of visual, audible, and/or haptic input requests, then the alerter system 100 may begin providing only visual, audible, or haptic requests.

The augmentation system may direct the alerter system 100 to change the frequency and/or type of input requests regardless of the speed at which the vehicle is moving. For example, the speed of the vehicle may change without impact on how the input requests change. The frequency and/or type of input requests may change in identical manners (or remain the same) even if the vehicle speeds up or slows down.

At 216, a determination is made as to whether operation of the powered system is to be changed. If the operator is not responding to the input requests and/or if the alertness of the operator (as determined at 210) is too low, then operation of the powered system may be changed. As a result, flow of the method 200 can proceed toward 218. But, if the operator is responding to the input requests (e.g., within the designated period of time) and/or if the alertness of the operator is not too low, then operation of the powered system may not be changed. As a result, flow of the method 200 can return toward 202 or optionally may terminate.

At 218, one or more responsive actions are implemented. For example, in response to the alertness of the operator being too low (e.g., as determined by the monitoring system 102 and/or based on a lack of response to input requests as determined by the alerter system 100), operation of the powered system being controlled by the operator may be automatically change. The monitoring system 102, alerter system 100, and/or augmentation system may automatically generate and communicate a control signal that causes a propulsion system of the vehicle to slow movement of the vehicle and/or that causes a brake system of the vehicle to engage and slow or stop movement of the vehicle.

In one embodiment, the control signal may direct a controller of the vehicle to switch from automatic control of movement of the vehicle to manual control of the vehicle. For example, responsive to the alertness score of the operator dropping below an upper designated threshold, the controller may automatically switch from automatically controlling movement of the vehicle to manual control of the vehicle. Optionally, the control signal may direct the controller of the vehicle to switch from manual control of the vehicle (e.g., control by the operator) to another automatic control of the vehicle. The automatic control may be a decreased or reduced operational mode, such as automatic control of the vehicle, but at a slower speed than previously moving under control of the operator, a slower speed than previously dictated by an energy management system (described below), etc. This can occur responsive to the alertness score of the operator dropping below a lower designated threshold. This can allow for the vehicle to continue operating but with decreased risk of damage to others or the vehicle relative to traveling at faster speeds and/or relative to operator control of the vehicle. Following 218, flow of the method 200 may then return toward 202 or may terminate.

Figure 3:
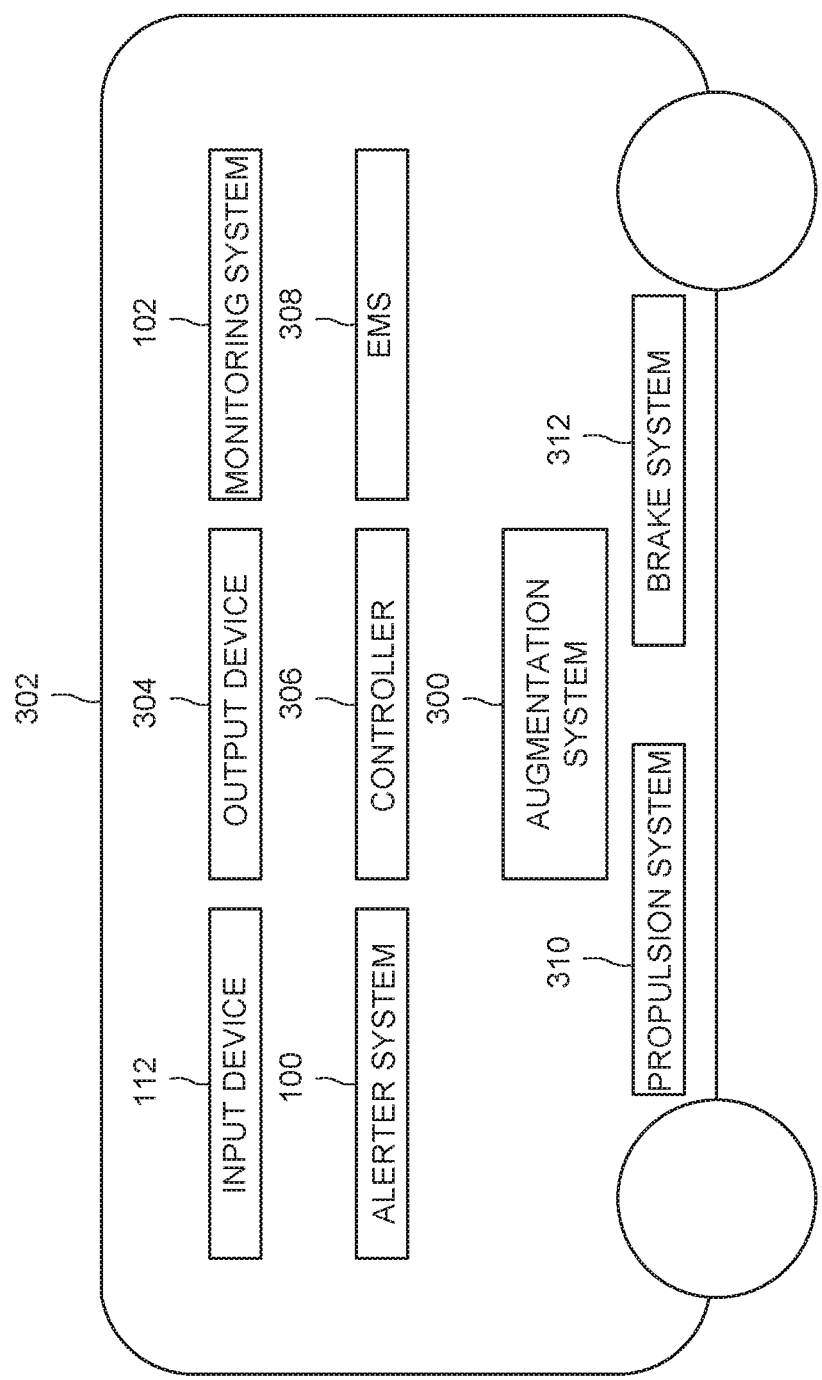
FIG. 3 illustrates one embodiment of an alerter augmentation system.

FIG. 3 illustrates one embodiment of an alerter augmentation system 300. The augmentation system 300 may be operably coupled with a powered system 302, such as by being communicatively coupled with the powered system 302 by one or more wired and/or wireless connections. The powered system 302 is illustrated as a vehicle, such as an automobile, rail vehicle, truck, bus, mining vehicle, marine vessel, aircraft, or other off-highway vehicle (e.g., a vehicle that is not designed for travel on public roadways and/or is not legally permitted for travel on public roadways). Alternatively, the powered system 302 may be a stationary system, such as a power plant, a facility where operators monitor a location (e.g., a security facility), etc. The augmentation system 300 can represent hardware circuitry that includes and/or is connected with one or more processors (e.g., microprocessors, integrated circuits, and/or field programmable gate arrays) that perform the operations described above. For example, the processors may determine the alertness of the operator from the alertness data output by the monitoring system 102, determine whether to change the input requests generated by the alerter system 100, and/or instruct the alerter system 100 to change the input requests, as described above.

The alerter system 100 and/or the monitoring system 102 can represent hardware circuitry that includes and/or is connected with one or more processors (e.g., microprocessors, integrated circuits, and/or field programmable gate arrays) that perform the operations described above. For example, the processors may generate control signals to direct one or more output devices 304 (e.g., the light generating devices 106, display device 108, vibration-generating or haptic devices, etc.) to provide the input requests, monitor and determine the alertness of the operator, generate and provide the alertness data to the augmentation system 300, determine whether the operator has responded to the input requests, etc., as described above.

A controller 306 of the powered system 302 represents hardware circuitry that includes and/or is connected with one or more processors (e.g., microprocessors, integrated circuits, and/or field programmable gate arrays) that control operation of the powered system 302. The controller 306 can receive input from the operator via the input device 112, can receive an operational plan from an energy management system 308 ("EMS" in FIG. 3), and/or receive a control signal from the alerter system 100 (and optionally the monitoring system 102 and/or augmentation system 300). Based on the received input, operational plan, and/or control signal, the controller 306 may generate instruction signals that are communicated to a propulsion system 310 and/or brake system 312 of the powered system 302. The instruction signals direct operation of the propulsion system 310 and/or brake system 312, such as by directing the propulsion system 310 to increase or decrease the speed of the powered system 302, directing the brake system 312 to engage or release brakes of the powered system 302, or the like.

The energy management system 308 represents hardware circuitry that includes and/or is connected with one or more processors (e.g., microprocessors, integrated circuits, and/or field programmable gate arrays) that determine the operational plan for the powered system 302. Optionally, the energy management system 308 is off-board or outside of the powered system 302. The operational plan dictates one or more operational settings of the powered system 302 for different times, different locations along one or more routes, and/or different distances along the one or more routes. The operational plan may designate speeds, throttle settings, brake settings, accelerations, etc., for the powered system 302 in order to reduce the fuel consumed and/or emissions generated by the powered system 302 while resulting in the powered system 302 arriving within a scheduled time period relative to the powered system 302 traveling according to other settings, such as by traveling at an upper speed limit of the route.

The propulsion system 310 represents one or more components that generate tractive effort to move the powered system 302. The propulsion system 310 can represent one or more engines, motors, propellers, etc. The brake system 312 represents one or more brakes of the powered system 302, such as air brakes, friction brakes, regenerative brakes (e.g., one or more of the motors of the propulsion system 310), etc.

In one embodiment, a system (e.g., an alerter augmentation system) includes one or more processors configured to determine an alertness of an operator of a vehicle system. The one or more processors also are configured to generate operator input requests that are separated in time by a temporal delay, the one or more processors configured to change one or more of the temporal delay between the input requests or a type of the input requests that are generated based at least in part on the alertness of the operator that is determined.

Optionally, the one or more processors determine the alertness of the operator based on one or more differences between a current operator behavior and a historical operator behavior.

Optionally, the one or more processors are configured to change the temporal delay between the input requests regardless of a moving speed of the vehicle system.

Optionally, the one or more processors are configured to change the temporal delay between the input requests by increasing the temporal delay between the successive input requests responsive to the alertness of the operator that is determined indicating that the operator is alert.

Optionally, the one or more processors are configured to determine that the alertness of the operator indicates that the operator is alert responsive to the alertness one or more of exceeding a designated threshold score or increasing from a previously determined alertness.

Optionally, the one or more processors are configured to change the temporal delay between the successive input requests by decreasing the temporal delay between the successive input requests responsive to the alertness of the operator indicating that the operator is less alert than a previous time.

Optionally, the one or more processors are configured to determine that the alertness of the operator indicates that the operator is less alert responsive to the alertness one or more of not exceeding a designated threshold score or decreasing from a previously determined alertness.

Optionally, the one or more processors are configured to change the type of the input requests by switching from visually providing the input requests to audibly providing the input requests.

Optionally, the one or more processors are configured to change the type of the input requests provided by the alerter system by switching from audibly providing the input requests to visually providing the input requests.

Optionally, the one or more processors are configured to automatically apply a brake of the vehicle system responsive to the alertness of the operator decreasing below a designated threshold score.

Optionally, the one or more processors are configured to automatically switch from automatic control of movement of the vehicle system to manual control of the movement of the vehicle system responsive to the alertness of the operator decreasing below a first designated threshold score.

Optionally, the one or more processors are configured to automatically switch from manual control of the movement of the vehicle system to reduced operation automatic control of the movement of the vehicle system responsive to the alertness of the operator decreasing below a smaller, second designated threshold score.

In one embodiment, a method (e.g., for augmenting operation of an alerter system) includes determining an alertness of an operator of a vehicle system using a monitoring system, and changing one or more of a temporal delay between successive input requests provided by an alerter system of the vehicle system or a type of the input requests provided by the alerter system based at least in part on the alertness of the operator that is determined.

Optionally, the alertness of the operator is determined based on one or more differences between a current operator behavior and a historical operator behavior.

Optionally, changing the temporal delay between the successive input requests occurs regardless of a moving speed of the vehicle system.

Optionally, changing the temporal delay between the successive input requests includes increasing the temporal delay between the successive input requests responsive to the alertness of the operator that is determined indicating that the operator is alert.

Optionally, the alertness of the operator indicates that the operator is alert when the alertness as determined by the monitoring system one or more of exceeds a designated threshold score or increases from a previously determined alertness.

Optionally, changing the temporal delay between the successive input requests includes decreasing the temporal delay between the successive input requests responsive to the alertness of the operator that is determined indicating that the operator is less alert than a previous time.

Optionally, the alertness of the operator indicates that the operator is less alert when the alertness as determined by the monitoring system one or more of does not exceed a designated threshold score or decreases from a previously determined alertness.

Optionally, changing the type of the input requests provided by the alerter system includes switching from visually providing the input requests to audibly providing the input requests.

Optionally, changing the type of the input requests provided by the alerter system includes switching from audibly providing the input requests to visually providing the input requests.

Optionally, the method also includes automatically applying a brake of the vehicle system responsive to the alertness of the operator that is determined decreasing below a designated threshold score.

Optionally, the method also includes automatically switching from automatic control of movement of the vehicle system to manual control of the movement of the vehicle system responsive to the alertness of the operator that is determined decreasing below a first designated threshold score.

Optionally, the method also includes automatically switching from manual control of the movement of the vehicle system to reduced operation automatic control of the movement of the vehicle system responsive to the alertness of the operator that is determined decreasing below a smaller, second designated threshold score.

In one embodiment, a system (e.g., an alerter augmentation system) includes one or more processors configured to automatically instruct an alerter system to generate requests for operator input at time intervals in order to maintain an alertness of an operator controlling a powered system. The one or more processors also are configured to direct the alerter system to one or more of change the time intervals between the requests or change a type of the requests responsive to a change in the alertness of the operator.

Optionally, the one or more processors are configured to direct the alerter system to increase a time delay between successive requests for operator input responsive to the alertness of the operator increasing and to direct the alerter system to decrease the time delay responsive to the alertness of the operator decreasing.

Optionally, the one or more processors are configured to direct a controller of the powered system to automatically change from manual control of the powered system to automatic control of the powered system responsive to a decrease in the alertness of the operator.

It is to be understood that the above description is intended to be illustrative, and not restrictive. For example, the above-described embodiments (and/or examples thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

What is claimed is:

1. A system comprising:
one or more sensors configured to obtain information regarding an alertness of an operator of a vehicle system and output a signal including the information; and
one or more processors configured to receive the signal and determine the alertness of the operator of the vehicle system, the one or more processors also configured to generate operator input requests that are separated in time by a dynamically changing temporal delay, the one or more processors configured to change a duration of the temporal delay based at least in part on the alertness of the operator that is determined.

2. The system of claim 1, wherein the one or more processors determine the alertness of the operator based on one or more differences between a current operator behavior and a historical operator behavior.

3. The system of claim 1, wherein the one or more processors are configured to change the duration of the temporal delay regardless of a moving speed of the vehicle system.

4. The system of claim 1, wherein the one or more processors are configured to increase the duration of the temporal delay between the input requests responsive to the alertness of the operator that is determined indicating that the operator is alert.

5. The system of claim 4, wherein the one or more processors are configured to determine that the operator is alert responsive to the alertness increasing from a previously determined alertness.

6. The system of claim 1, wherein the one or more processors are configured to shorten the duration of the temporal delay responsive to the alertness of the operator indicating that the operator is less alert than a previous time.

7. The system of claim 6, wherein the one or more processors are configured to determine that the operator is less alert responsive to the alertness decreasing from a previously determined alertness.

8. The system of claim 1, wherein the one or more processors are configured to change a type of the input requests based on the alertness of the operator by switching from visually providing the input requests to audibly providing the input requests.

9. The system of claim 1, wherein the one or more processors are configured to change a type of the input requests based on the alertness of the operator by switching from audibly providing the input requests to visually providing the input requests.

10. The system of claim 1, wherein the one or more processors are configured to automatically apply a brake of the vehicle system responsive to the alertness of the operator decreasing below a designated threshold score.

11. The system of claim 1, wherein the one or more processors are configured to automatically switch from automatic control of movement of the vehicle system to manual control of the movement of the vehicle system responsive to the alertness of the operator decreasing.

12. The system of claim 1, wherein the one or more processors are configured to automatically switch from manual control of the movement of the vehicle system to reduced operation automatic control of the movement of the vehicle system responsive to the alertness of the operator decreasing.

13. A method comprising:
obtaining, by one or more sensors, information regarding an alertness of an operator of a vehicle system;
outputting, by the one or more sensors, one or more signals including the information;
receiving, by one or more processors, the one or more signals;
determining, by the one or more processors, an alertness of the operator of the vehicle system; and
changing, by the one or more processors, a duration of a temporal delay between successive input requests provided by an alerter system of the vehicle system based at least in part on the alertness of the operator that is determined.

14. The method of claim 13, wherein the alertness of the operator is determined based on one or more differences between a current operator behavior and a historical operator behavior.

15. The method of claim 13, wherein changing the temporal delay between the successive input requests occurs regardless of a moving speed of the vehicle system.

16. The method of claim 13, wherein the duration of the temporal delay is increased responsive to the alertness of the operator indicating that the operator is alert.

17. The method of claim 16, wherein the alertness of the operator indicates that the operator is alert when the alertness as determined by the monitoring system one or more of exceeds a designated threshold score or increases from a previously determined alertness.

18. A system comprising:
one or more sensors configured to obtain information regarding an alertness of an operator of a vehicle system and output a signal including the information; and
one or more processors configured to receive the signal, and automatically instruct an alerter system to generate requests for operator input at time intervals to maintain an alertness of an operator controlling a powered system, the one or more processors also configured to direct the alerter system to change the time intervals between the requests and to change a type of the requests based on a change in the alertness of the operator.

19. The system of claim 18, wherein the one or more processors are configured to direct the alerter system to increase a time delay between successive requests for operator input responsive to the alertness of the operator increasing and to direct the alerter system to decrease the time delay responsive to the alertness of the operator decreasing.

20. The system of claim 18, wherein the one or more processors are configured to direct a controller of the powered system to automatically change from manual control of the powered system to automatic control of the powered system responsive to a decrease in the alertness of the operator.

* * * * *